(12) United States Patent
Kamiyama et al.

(10) Patent No.: US 6,186,948 B1
(45) Date of Patent: Feb. 13, 2001

(54) ULTRASONIC DIAGNOSTIC APPARATUS

(75) Inventors: Naohisa Kamiyama; Yoichi Ogasawara, both of Tochigi-ken (JP)

(73) Assignee: Kabushiki Kaisha Toshiba, Kawasaki (JP)

( * ) Notice: Under 35 U.S.C. 154(b), the term of this patent shall be extended for 0 days.

(21) Appl. No.: 09/300,386

(22) Filed: Apr. 27, 1999

(30) Foreign Application Priority Data

Oct. 7, 1998 (JP) .................................................. 10-285219

(51) Int. Cl.$^7$ ...................................................... H61B 8/00
(52) U.S. Cl. ........................................... 600/443; 128/916
(58) Field of Search ................................... 600/437, 440, 600/443, 447; 128/916

(56) References Cited

U.S. PATENT DOCUMENTS

| | | | |
|---|---|---|---|
| 5,353,354 | * 10/1994 | Keller et al. ............................ | 382/6 |
| 5,413,106 | * 5/1995 | Fujita et al. ...................... | 128/916 X |
| 5,485,842 | * 1/1996 | Quistgaard ........................ | 128/916 X |
| 5,546,807 | 8/1996 | Oxaal et al. . | |
| 5,682,895 | * 11/1997 | Ishiguro ................................ | 600/440 |
| 5,776,067 | * 7/1998 | Kamada et al. ................... | 128/916 X |
| 5,872,571 | * 2/1999 | Arling ................................... | 345/427 |
| 5,993,391 | * 11/1999 | Kamiyama ....................... | 128/916 X |

* cited by examiner

Primary Examiner—Francis J. Jaworski
(74) Attorney, Agent, or Firm—Oblon, Spivak, McClelland, Maier & Neustadt, P.C.

(57) ABSTRACT

An ultrasonic diagnostic apparatus wherein an echo signal produced by scanning an ultrasonic beam at a three dimensional region is received and a two dimensional cross sectional image and three dimensional information based on the echo signal are obtained. A display is operable in a first mode in which only the cross sectional image is displayed, a second mode in which only the three dimensional information is displayed, and a third mode in which the three dimensional information overlapped with said cross sectional image is displayed. The three dimensional information at least includes a portion of the two dimensional cross sectional image, and preferably adjacent front side and rear side regions. In a preferred embodiment, the three dimensional information is color doppler information and the two dimensional cross sectional image is a gray scale image, and the areas of the cross sectional surfaces in which the color doppler information is obtained in a direction perpendicular to the front and back of the gray scale two dimensional cross sectional image become smaller as the distance from the gray scale two dimensional cross sectional image increases.

22 Claims, 8 Drawing Sheets

ULTRASONIC DIAGNOSTIC APPARATUS

CROSS REFERENCE TO RELATED APPLICATIONS

This application claims benefit of priority to Japanese Patent Application No. P10-285219 filed Oct. 7, 1999, the entire disclosure of which is incorporated by reference herein.

BACKGROUND OF THE INVENTION

1. Field of the Invention

The present invention relates to an ultrasonic diagnostic apparatus for real time display of three dimensional information of a diagnosed portion of an object

2. Discussion of the Background

In general, in the conventional ultrasonic diagnostic system, a predetermined cross sectional surface is scanned by an ultrasonic beam transmitted from an ultrasonic probe in the form of a one dimensional array of piezoelectric transducers and a cross sectional image based on two dimensional information is displayed. On the other hand, experiments have been performed to obtain three dimensional picture image information (i.e., volume image) by operating the ultrasonic probe in a three dimensional space. In an ultrasonic diagnostic apparatus, the display of three dimensional image has been expected to develop a new approach to diagnosis. Research has proceeded to changing a direction of an ultrasonic beam by manually or mechanically moving a convex probe and a linear array probe for an abdominal region, and using a multi plane probe having a mechanism for rotating an electronic sector for an oesophagus region.

In such a three dimensional ultrasonic diagnostic apparatus, three dimensional scanning in order to obtain three dimensional information is very time consuming compared to cross sectional scanning in a conventional two dimensional ultrasonic diagnostic apparatus. In the case of detecting an object exhibiting quick movement, such as a heart, scanning can not follow such a quick movement. A display of such an object is sometimes distorted. In the case of an object exhibiting slow movement, such as an abdominal region using a fixed probe is insufficient, yet if a moving probe is used, and the moving speed of the probe is not constant, the display of the abdominal region is greatly distorted.

Therefore, an ultrasonic diagnostic apparatus has been developed including a two dimensional probe having an electronic scanning two dimensional phased array of piezoelectric transducers and an ultrasonic probe having a function of electronically scanning three dimensional space with a ultrasonic beam so that a three dimensional volume image is scanned at a frame rate nearly 30 frame/second (real time).

The three dimensional volume image provides information along a front-rear direction which can not be obtained in a conventional two dimensional cross sectional image and provides a capability to observe a diagnosed portion at any point of sight. However, in so doing, it is necessary to change and rotate an observed cross sectional surface. Such a capability makes it easy to reproduce a picture image at one moment and to reproduce an animation image repeatedly at several seconds. However, in the case of diagnosing an object using a continuous animation image such as an ultrasonic diagnostic image, it is again difficult to process the entire three dimensional image information due to limitations on processing speed. However, an operation of changing and rotating an observed cross sectional surface is not necessary for the entire three dimensional image.

In an ultrasonic diagnostic apparatus for scanning/displaying a three dimensional volume image at real time, a request to observe an image at a frame rate substantially equal to that of a conventional two dimensional cross sectional image at a cross sectional surface would be considered in the case of displaying a three dimensional volume image. In the case of always three dimensionally scanning and reconstructing a two dimensional cross sectional image based on a received three dimensional information, a resolution level of three dimensional information is not considered of great importance in order to maintain a frame rate at real time. Therefore, an amount of ultrasonic energy for three dimensionally scanning is more than that for a conventional two dimensional ultrasonic diagnostic apparatus which obtains two dimensional image information of the same quality as that of the conventional two dimensional ultrasonic diagnostic apparatus. This presents a safety problem.

As described above, a conventional three dimensional ultrasonic diagnostic apparatus has a drawback of not displaying the entire three dimensional information in real time and a drawback of needing more ultrasonic energy than that of a conventional apparatus in order to display a two dimensional cross sectional image.

SUMMARY OF THE INVENTION

Accordingly, the objects of the present invention are to produce a cross sectional image of an object with improved quality compared to that of the conventional two dimensional ultrasonic diagnostic apparatus, to form a three dimensional image about a three dimensional region including at least the cross sectional image, and to provide an ultrasonic diagnostic apparatus for displaying the three dimensional image overlapped on the cross sectional image.

These and other objects are achieved according to the present invention by providing a new and improved ultrasonic diagnostic apparatus wherein a cross sectional image having an echo brightness with a quality equal to or greater than that of the conventional ultrasonic diagnostic apparatus is displayed, a three dimensional image is overlapped with a cross sectional image, and the overlapped image is displayed by obtaining three dimensional information about a three dimensional region including at least the cross sectional surface, without reducing a frame rate in three dimensionally scanning the three dimensional region. In the case of mainly displaying the cross sectional image, according to the method of the present invention, the three dimensional image is displayed standing in bold relief on the cross sectional image and information along a front-rear direction can be observed in order to promote accurate diagnosis.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
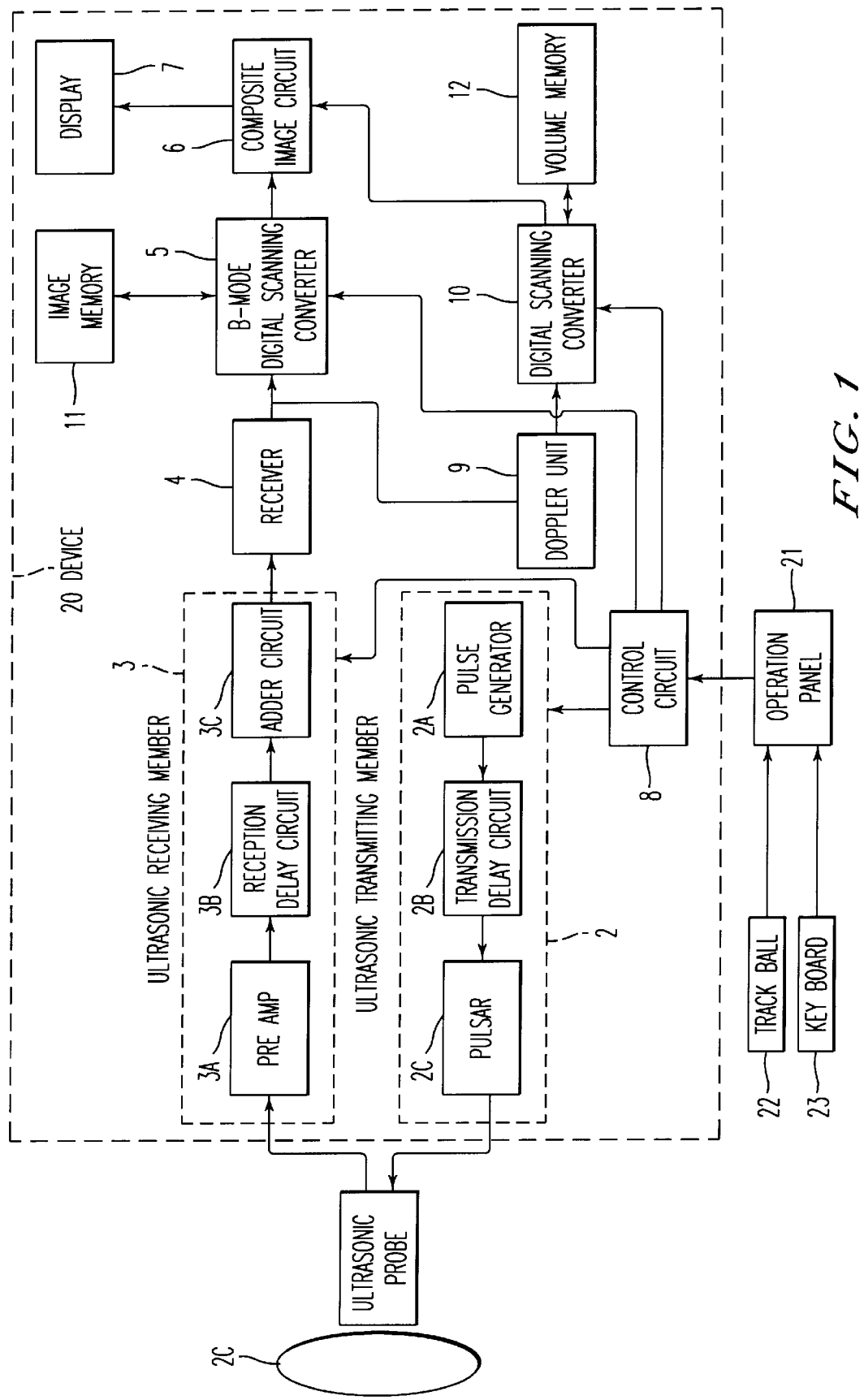
FIG. 1 is a block diagram of a first embodiment of an ultrasonic diagnostic apparatus according to the present invention.

Referring now to the drawings, wherein like reference numerals designate identical or corresponding parts throughout the several views, and more particularly to FIG. 1 thereof, a first embodiment of an ultrasonic diagnostic apparatus according to the present invention. includes an electronic scanning two-dimensional phased array ultrasonic piezoelectric transducer, ultrasonic probe 1 which three dimensionally transmits and scans an ultrasonic beam toward a three-dimensional space of an interior of an body of an detected object P through a skin surface of the body.

The ultrasonic probe 1 is driven in accordance with a predetermined scanning method and a device 20 for processing a signal received from the ultrasonic probe 1 is connected to the ultrasonic probe 1. A track ball 22 and a keyboard 23 and so on are connected to the device 20. Further, an operation panel for displaying instruction information from an operator is connected to the device 20. In a conventional art, input devices such as the track ball 22, the keyboard 23 and so on select operating conditions depending on the devices and region of interest (hereinafter, referred to as "ROI") . In the present invention, operating conditions can be selected and changed in a manner similar to that of conventional devices.

The device 20 includes an ultrasonic transmission member 2 and an ultrasonic receiving member 3 connected to the ultrasonic probe 1.

The ultrasonic transmission member 2 includes a pulse generator 2A, a transmission delay circuit 2B and a pulsar 2C, wherein a pulse-shaped ultrasonic beam is generated from the ultrasonic probe 1 and three-dimensionally scanned. The interior of the body of object P is three dimensional scanned by the beam. In the ultrasonic probe 1 having a two-dimensional array, the transmission delay circuit 2B controls delay times in order to control a focus point for receiving echo signal transmitted from any direction in space, a cross sectional image and sound field in a vertical direction. Thus, compared to a one-dimensional array probe, an echo signal having a more restricted focus region can be obtained.

Figure 2A:
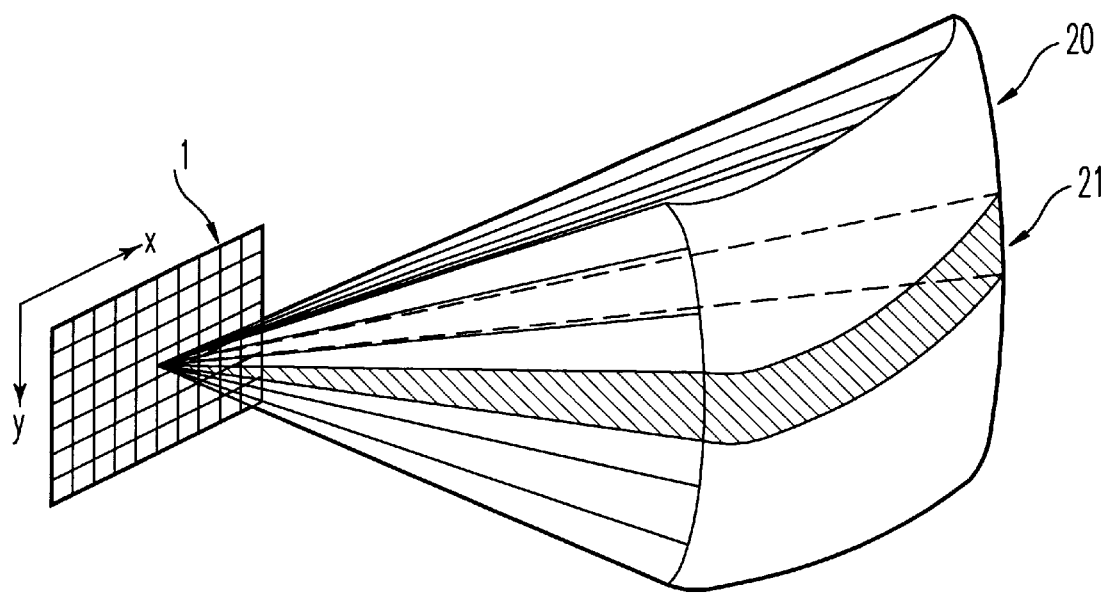
FIGS. 2(*a*) and 2(*b*) are schematic illustrations of a model of three dimensional and two dimensional cross sectional sound fields, separately, in the ultrasonic diagnostic apparatus according to the present invention.
Figure 2B:
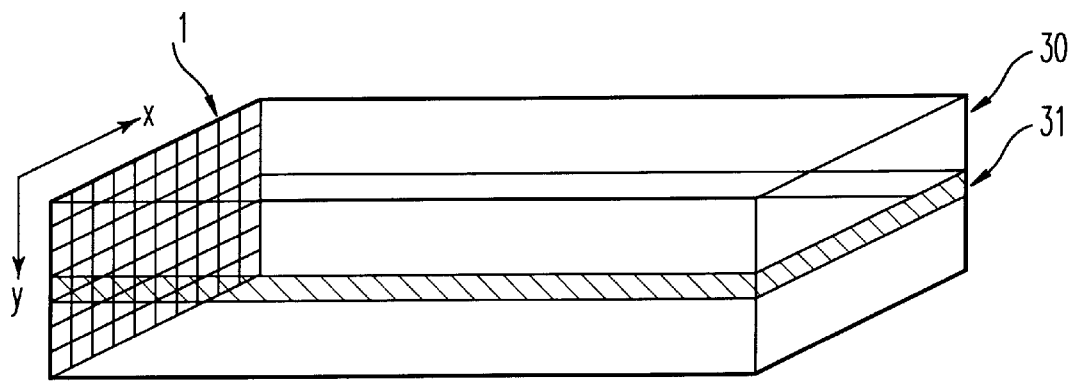

FIG. 2(a) and FIG. 2(b) shows models of three- and two-dimensional sound fields obtained by scanning in accordance with a sector method and a linear method, respectively. The two-dimensional phased array ultrasonic probe 1 receives three-dimensional echo signal simultaneously so that three-dimensional information can be obtained by two-dimensional beam forming. The two-dimensional phased array ultrasonic probe 1 is utilized to improve the picture image of two-dimensional image. In a conventional one-dimensional array probe, a sound field in a sound lens direction can not be changed. On the other hand, in the present invention, beam forming in a y-axis can be operated by the two dimensional probe so that a spreading beam sound field in a lens direction (y-axis direction) can be controlled. Thus, picture image quality can be considerably improved. Three dimensional sound fields 20, 30 can be simultaneously received by all the piezoelectric transducers of the two dimensional phased array ultrasonic probe 1. Two dimensional cross sectional sound fields 21 and 31 are formed as a dimensional beam by operating piezoelectric transducers aligned on one row in the x-axis direction of the ultrasonic probe 1 and transducers aligned on a plurality of rows for controlling sound field spreading in a lens direction (y-axis direction). The two dimensional cross sectional sound fields 21 and 31 can be formed along any inclined direction besides the x-axis direction and the y-axis direction by controlling delay time.

An echo signal output from all the piezoelectric transducers or a predetermined number of piezoelectric transducers of the ultrasonic probe 1 in every channel is received at the ultrasonic receiving member 3. The echo signal in every channel is amplified by an preamplifier 3A, delayed by the delay circuit 3B for a delay time necessary to determine a receiving directivity, and added by an adder 3C. By adding delay times, reflective echo components, from a direction of which the receiving directivity is added, is emphasized. An ultrasonic beam having total directivity performance is formed by combining a transmitting directivity controlled by the transmission delay circuit 2B and a receiving directivity controlled by the receiving delay circuit 3B.

An output from the ultrasonic receiving member 3 is supplied through a receiving member 4 including a logarithmic amplifier, an envelope detecting circuit and an analog-digital converter (not shown) to a B-mode (cross sectional image) digital scanning converter 5 and a driving unit 9. The B-mode digital scanning converter 5 converts raster signal rows of ultrasonic scanning to B mode cross sectional image information (hereinafter, referred to as a "B mode image") by arranging the raster signal rows in a video format.

An image memory 11 for storing the B mode image is connected to the B-mode digital scanning converter 5. The image memory 11 includes a semiconductor memory for memorizing a signal from the B-mode digital scanning converter 5 (in either or both of the form of a raster signal row of ultrasonic scanning and/or a raster signal row in a video format). An output from the B-mode digital scanning converter 5 is supplied to a composite circuit 6.

An output from the driving unit 9 is supplied to a three dimensional (3D) picture image digital scanning converter 10. The driving unit 9 detects a Doppler signal in order to calculate blood fluid speed or power information. In the present invention, the 3D image digital scanning converter 10 reconstructs a three dimensional picture image for indicating information of blood fluid speed by obtaining three dimensional information of a color Doppler signal and a three dimensional picture image is mapped on a two dimensional plane by utilizing a preferable two dimensional mapping method (to form a bird's-eye view) The reconstructed image is overlapped with the B mode picture image in the composite image circuit 6.

A volume memory 12, similar as the image memory 11, for storing the three dimensional picture image is connected to the 3D image digital scanning converter 10. The volume memory 12 includes a semiconductor memory for memorizing a signal from the 3D image digital scanning converter 5 (either or both of three dimensional information of color Doppler and three dimensional information of blood fluid image). The memorized information stored in the image memory 11 and the volume memory 12 can be picked up by an operator after finishing medical examination. In such a case, the picked-up information is input to a display member 7 through the digital scanning converters 5, 10 and the composite image circuit 6.

The composite image circuit 6 combines the picture image signals from both digital scanning converters 5 and 10 and to produce an overlapped image, and further overlaps a video signal, for display on the display 7. The video signal includes selected parameter information supplied from a host CPU (not shown) for display adjacent to the picture image or selected parameter information overlapped on the picture image. A control circuit 8, to which various control instruction signals are supplied from an operation panel 21, is connected to the ultrasonic transmission member 2, the ultrasonic receiving member 3, the B-mode digital scanning converter 5 and the 3D image digital scanning converter 10.

Operation of the first embodiment is next described. In this embodiment, B-mode two dimensional scanning and color Doppler three dimensional scanning are operated together. Each scanning operation is described hereinafter.

B-mode Two Dimensional Scanning

First, the raster density of the ultrasonic beam is predetermined according to the present invention so that B-mode cross sectional image photographed by the apparatus of the present invention can have a quality of picture image resolution equal to or greater than that of a picture image photographed by a conventional B-mode apparatus. Two dimensional scanning is operated by two dimensional beam forming with piezoelectric transducers aligned in an x-axis direction of a two dimensional array of piezoelectric transducers of the ultrasonic probe 1. In addition to the cross sectional surface including piezoelectric transducers aligned on some rows in x-axis direction, it is possible to obtain a picture image of a cross sectional surface in any inclined direction besides the x- and y- axis directions by controlling transmission delay amount. In such a case, an operator can select and adjust an angle with respect to a photographed cross sectional surface by operating the keyboard 23 and the track ball 22 on the operation panel 21.

Color Doppler Three Dimensional Scanning

Similar to a conventional two dimensional color Doppler ultrasonic diagnostic apparatus, color Doppler scanning is operated together with B-mode scanning. In contrast to the conventional apparatus, however, in the first embodiment according to the present invention, the color Doppler scanning operates not only two dimensional scanning for a B-mode cross sectional surface but also three dimensional scanning for a plurality of cross sectional surfaces. The number of cross sectional surfaces is not as many as that of a conventional three dimensional volume scanning in which each cross sectional surface is a square region and scanned with the same resolution level. In the present invention, the number of the cross sectional surfaces is a few and the scanned volume is a small region (a typical maximum length is several cm) including the B-mode scanned cross sectional surface.

Figure 3:
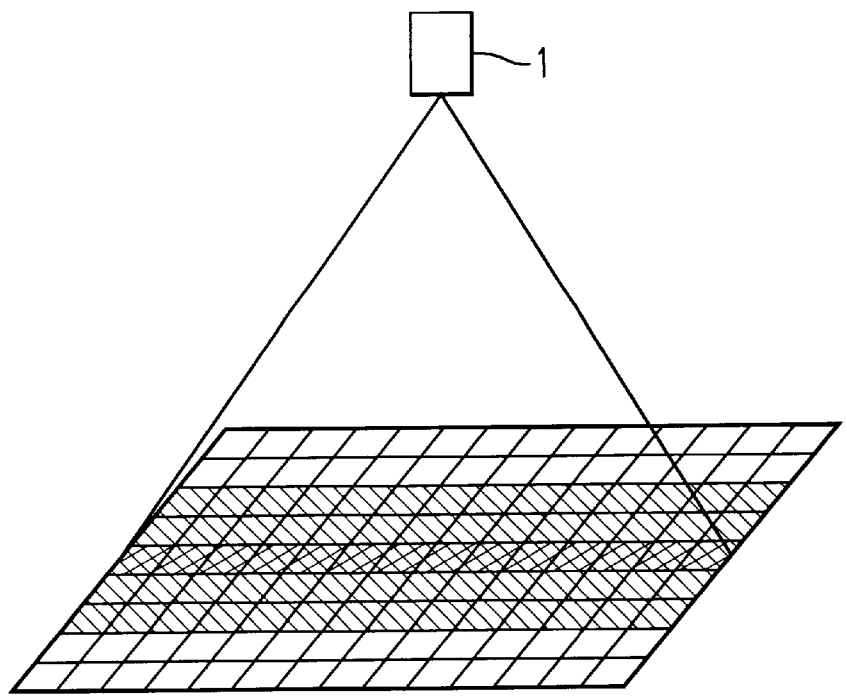
FIG. 3 is a schematic illustration of one example of a scanned area of B-mode two dimensional scanning/color Doppler three dimensional scanning according to the first embodiment of the ultrasonic diagnostic apparatus according to the present invention.

For example, as shown in FIG. 3, color Doppler three dimensional scanning is operated only for a restricted area (indicated by lines inclined from left-upper to right-lower) wherein a thickness of a reference B-mode cross sectional image (indicated by lines inclined from right-upper to left-lower) is several cm along a front-rear direction. By controlling three dimensional scanning to a limited area, a frame rate very close to real time can be accomplished without reducing the quality of picture image.

Figure 4:
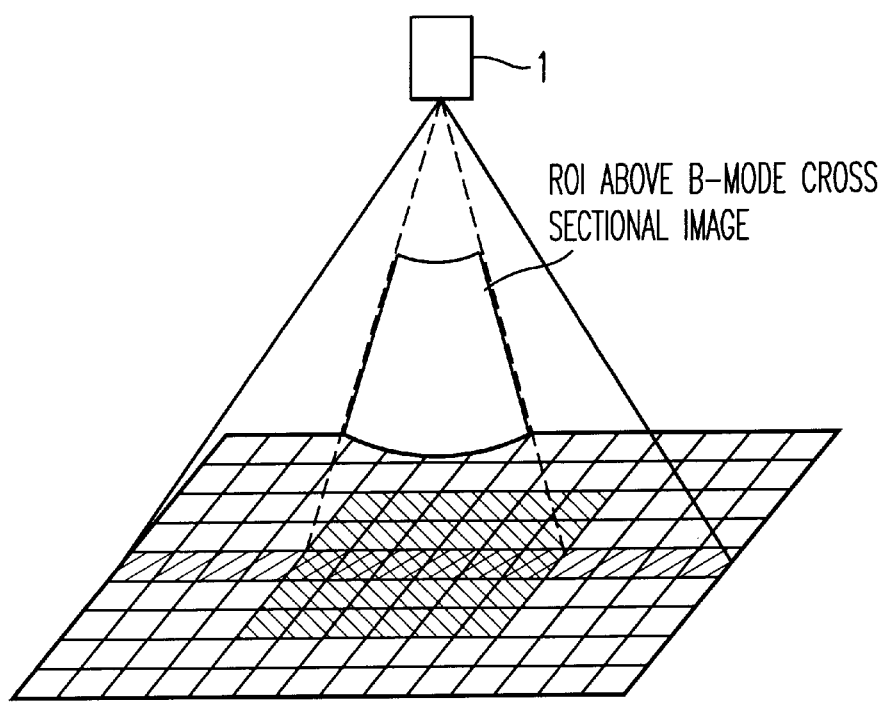
FIG. 4 is a schematic illustration of another example of a scanned area of B-mode two dimensional scanning/color Doppler three dimensional scanning of the first embodiment of the ultrasonic diagnostic apparatus according to the present invention.

In general, an ROI is provided at a part of a B-mode cross sectional image in order to obtain blood fluid information at the ROI. In such a case, as shown in FIG. 4, scanning may be limited to a restricted area corresponding to the size of an ROI wherein a thickness of a reference B-mode cross sectional image (indicated by lines inclined from right-upper to left-lower) is several cm along a front-rear direction.

Figure 5:
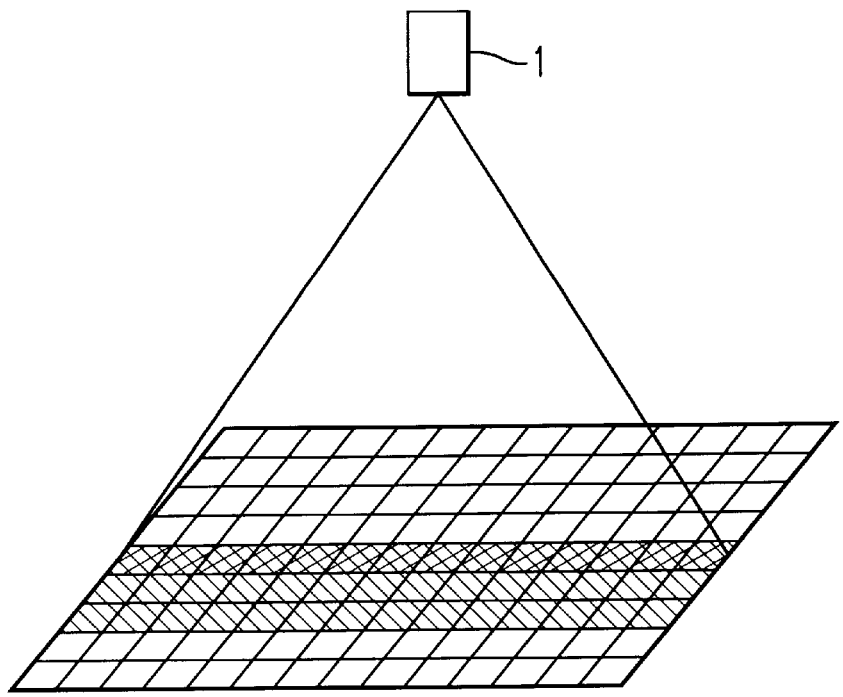
FIG. 5 is a schematic illustration of another example of a scanned area of 3-mode two dimensional scanning/ B-mode two dimensional scanning/color Doppler three dimensional scanning of the first embodiment of the ultrasonic diagnostic apparatus according to the present invention.

As shown in FIG. 5, scanning may be limited to a restricted area where a front-side thickness (visible side) of a B-mode cross sectional image is several cm. By combining the cases as shown in FIG. 4 and FIG. 5, scanning may be limited to a restricted area with a size corresponding to an ROI and a front-side thickness of a B-mode cross sectional image of several cm.

Figure 6:
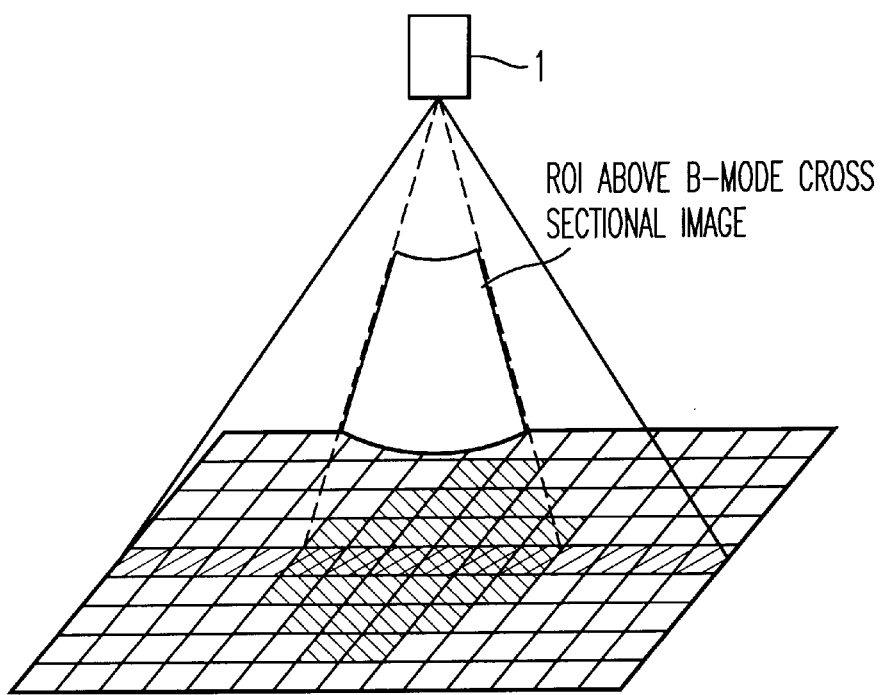
FIG. 6 is a schematic illustration of another example of scanned area of B-mode two-dimensional scanning/color Doppler three dimensional scanning of the first embodiment of the ultrasonic diagnostic apparatus according to the present invention.

Although the above described scanning scans a region of a B-mode cross sectional image having an uniform thickness, a color Doppler three dimensional scanning region need not necessarily have an uniform thickness along a direction perpendicular to the B-mode cross sectional image. For example, as shown in FIG. 6, the thickness of a central portion of the ROI may be greater than the thickness of a peripheral portion.

Echo information obtained by performing the two scanning methods together results in three dimensional volume data, that is, blood fluid information, derived at a region having a thickness of several cm by means of a two dimensional cross sectional image obtained by B-mode scanning and a two dimensional cross sectional image of the same several cm thick region obtained by color Doppler scanning. Various combinations can be considered in composite forms of the two scanning methods. If B-mode scanning is inserted while the color Doppler scanning method is operated, the insertion of the B mode scanning may be processed periodically or randomly.

The three dimensional volume data is Doppler-analyzed by the Doppler unit 9 to show color information indicating blood fluid. Then, the color information is reconstructed in a stereoscopic image by the 3D digital scanning converter 10. A picture image shown at a predetermined point of sight (bird's-eye view) is calculated by a known method such as the MIP method in order to form a three dimensional picture image. The three dimensional picture image is combined with the B mode picture obtained by the B-mode digital scanning converter 5 in The composite image circuit 6 and the combined image is displayed on the display member 7.

Figure 7A:
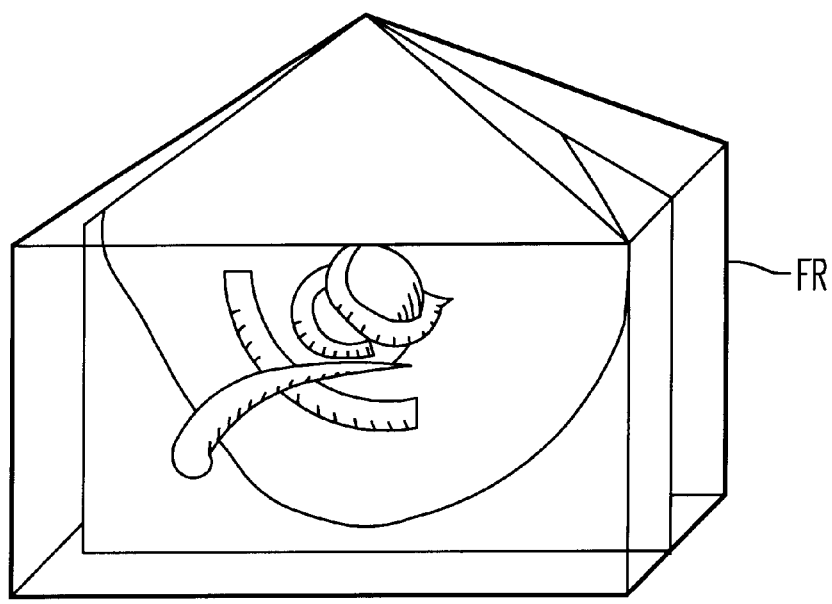
FIGS. 7(a) and 7(b) are schematic illustrations of one example of overlapping a B-mode cross sectional image with a color three dimensional image in the first embodiment of the ultrasonic diagnostic apparatus according to the present invention.

As shown in FIG. 7(a), The composite image circuit 6 overlaps a color three-dimensional image on a B-mode cross sectional image. In such a case, it is necessary to give appearance of a thickness along a front-rear direction of the color picture image. Therefore, as shown in FIG. 7(a), it is preferable to display a bird's eye view picture image at an upper point of sight with respect to a B-mode cross sectional surface. In the case, it is useful to display a supplement frame FR in order to indicate a picture image displayed by a bird's-eye view. However, the point of sight (bird's eye view) is not limited to an upper portion with respect to a B-mode cross sectional image but may also be displayed at a lower point of sight.

Several methods for overlapping a B mode cross sectional image and a color three-dimensional image are considered. For example, (i) blood fluid information appearing at the front side of the B mode cross sectional image is only displayed as a three-dimensional image, and (ii) all the blood fluid information appearing at the front side and the rear side of the B mode cross sectional image are displayed by displaying the B mode image transparently.

Figure 7B:
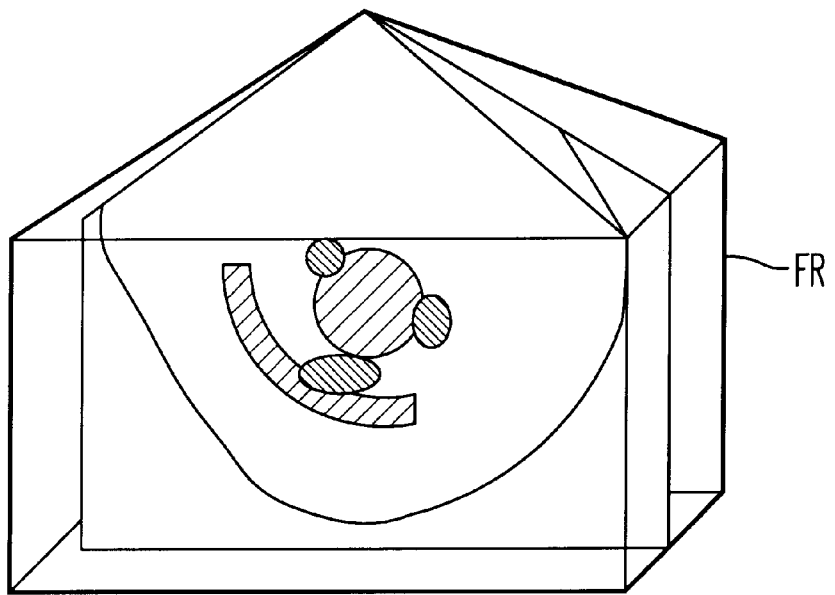

In one case according to the present invention, a first display in which a B mode cross sectional image is overlapped with a color three-dimensional image, a second display in which only a conventional B mode cross sectional image is displayed, and a third display in which the conventional B mode cross sectional image is overlapped with a color Doppler cross sectional image, can be switched momentarily in accordance with an instruction of an operator through an operation panel. FIG. 7(b) shows an image for displaying only a conventional B mode cross sectional image. Upon comparing the former case and the latter case, there is little difference in a point of a displayed cross sectional image so that an operator can switch a display very smoothly since a display type and an operation method are not much changed.

Next, an example of a clinical operation of an embodiment according to the present invention will be explained. For example, an operation for diagnosing hepatic cancer will be explained. First, a diseased area (such as tumor) is detected in a B mode cross sectional image. Of course, the B mode cross sectional image at the lowest has a resolution level the same as that of a conventional picture image. If the diseased area is found, the display is switched from B mode to color Doppler mode in order to observe whether there is blood fluid surrounding the tumor portion. If blood fluid flowing into the tumor portion is found, it is judged that a blood vessel gives nutrition to the tumor portion and the diseased area is deeply doubted as hepatic cancer. If a display is switched to a mode of overlapping B-mode cross sectional image and color three dimensional image, blood vessels surrounding the tumor portion can be displayed stereoscopically while a cross sectional image of the diseased area is displayed as a B-mode cross sectional image. Upon comparing the overlapped display according to the present invention with a conventional cross sectional image, relative positions of displayed elements can be shown more accurately in the present invention. Usually, screening and ultrasonic diagnosis of hepatic cancer involve a tumor which is less than 4 cm in length. In the case of displaying a cross sectional surface of a tumor portion having a maximum diameter in a B mode cross sectional image, a thickness of a three dimensional scanning area is 4 cm (2 cm at a front side of the cross sectional image and 2 cm at a rear side), enough to operate a color Doppler mode.

As described above, in the first embodiment according to the present invention, one cross sectional surface is two dimensionally scanned with a resolution level the same as that of the conventional scanning in order to obtain a B mode cross sectional image. In addition, a blood fluid image is obtained by three dimensionally scanning a three dimensional region, which is smaller than an area in a conventional scanning, at a substantially real time frame rate. The blood fluid image is displayed in bold relief on the B mode cross sectional image so that relative position along a front-rear direction can be. Accurate diagnosis thereby becomes possible.

In the following discussion, a second embodiment of an ultrasonic diagnostic apparatus according to the present invention will be described. Elements of the second embodiment corresponding to those of the first embodiment use the same numerals and a detailed explanation thereof is omitted.

Figure 8:
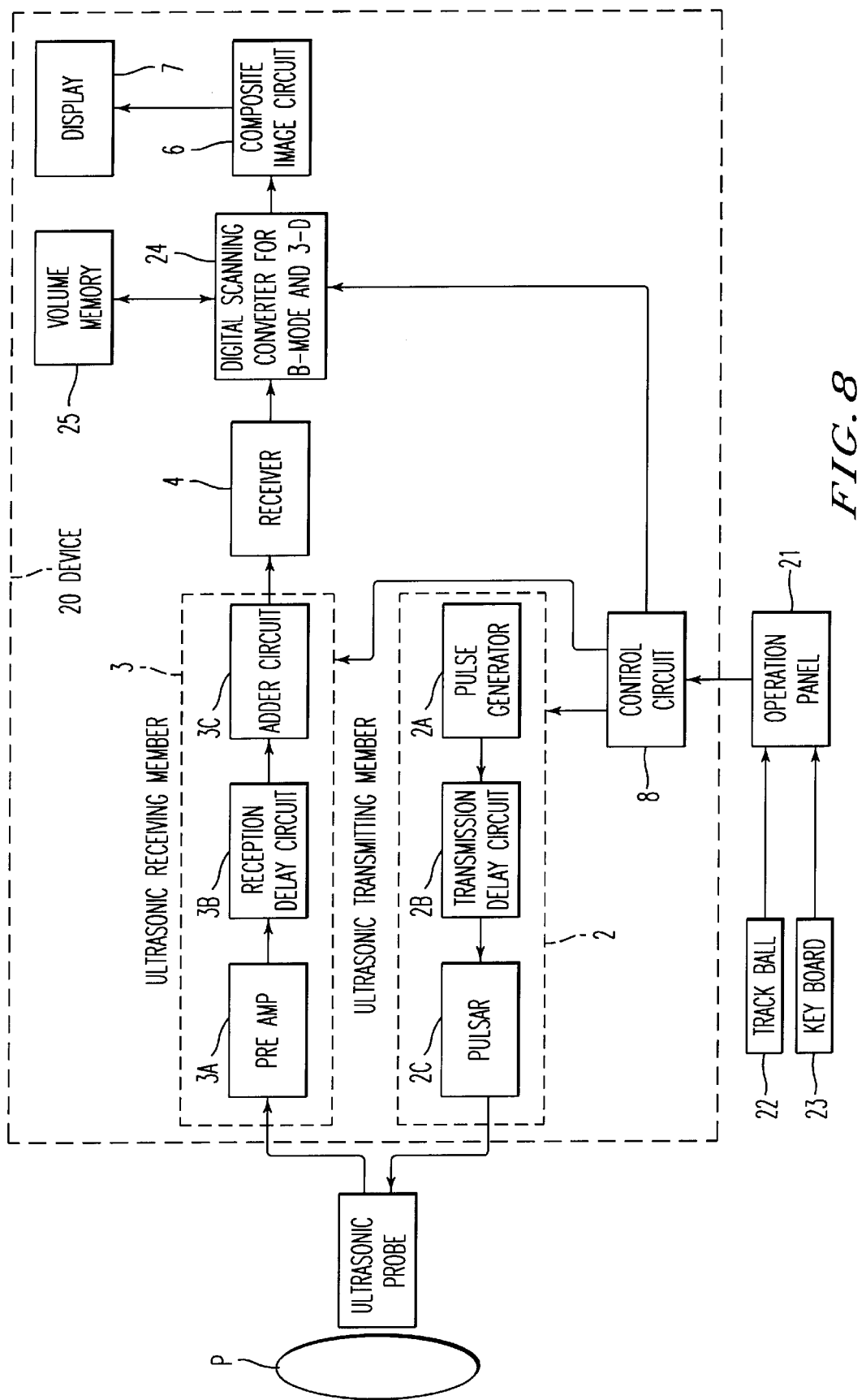
FIG. 8 is a block diagram of a second embodiment of an ultrasonic diagnostic apparatus according to the present invention.

FIG. 8 shows a block diagram of the second embodiment of an ultrasonic diagnostic apparatus. In the first embodiment, a color Doppler image is overlapped on a B mode cross sectional image. In the second embodiment, a color Doppler image is not utilized. Thus, the Doppler unit 9, the 3D digital scanning converter 10 and a volume memory 12 are omitted in the second embodiment. A B mode digital scanning converter 5, a B mode/3D digital scanning converter 24 instead of the image memory 11 and a volume memory 25 are provided in the second embodiment and a three dimensional volume image is reconstructed based on cross sectional images of a plurality of cross sectional surfaces.

Figure 9:
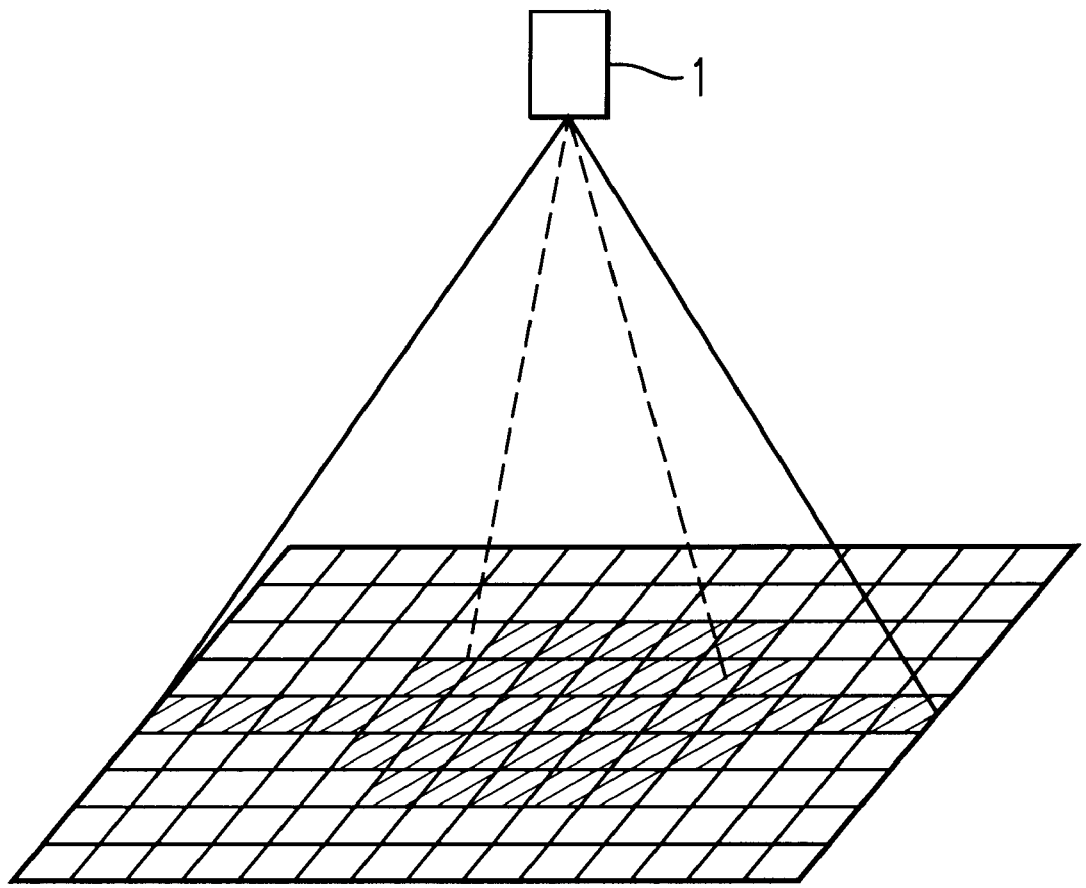
FIG. 9 is a schematic illustration of one example of scanned area of B-mode two dimensional scanning and color Doppler three dimensional scanning according to the second embodiment of the ultrasonic diagnostic apparatus according to the present invention.
Figure 10A:
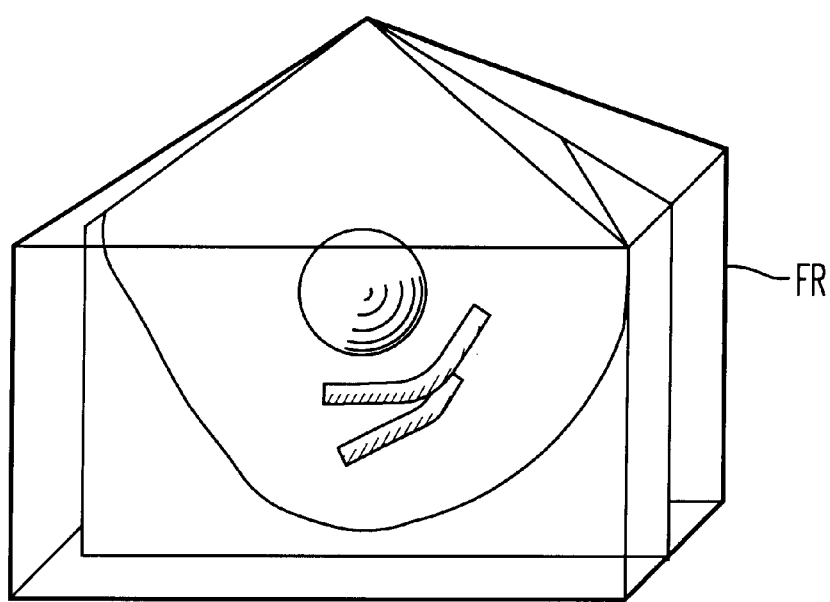
FIGS. 10(a) and 10(b) are schematic illustrations of one example for overlapping B-mode cross sectional image with color three dimensional image in the second embodiment of the ultrasonic diagnostic apparatus according to the present invention.
Figure 10B:
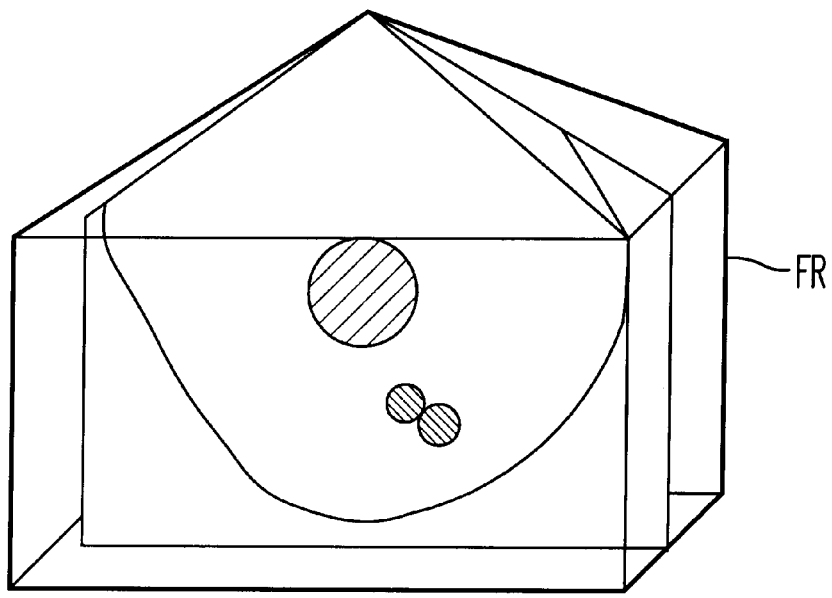

Thus, as shown in FIG. 9, a B-mode cross sectional image is obtained by two dimensionally scanning one cross sectional surface with a resolution the same as that of a conventional resolution. Further, data of a plurality of cross sectional images is obtained by scanning a plurality of the cross sectional surfaces in a scanned area which is smaller than that of a conventional three dimensional scanning. A picture image shown at a predetermined point of a sight (three dimensional image) is formed by utilizing the data of the plurality of cross sectional images in accordance with MIP (maximum (or minimum) intensity projection method. The three dimensional image is composed with the B-mode image in the composite image circuit 6 and the composed image is displayed at the display 7. As shown in FIG. 10(a), a diseased area can be observed stereoscopically in the B-mode cross sectional image. FIG. 10(b) shows only a conventional B-mode cross sectional image. In the embodiment, an operator can momentarily switch between a normal B mode cross sectional display and a display in which a B-mode cross sectional image is overlapped with a B mode stereoscopic image by utilizing an operation panel. For example, a cross sectional image of a diseased area having the maximum diameter is first displayed and a stereoscopically shape and structure of the diseased area can be observed by switching the mode according to the present invention. A three dimensional scanning area of the second embodiment can be properly selected in a manner similar to that described in regard to the first embodiment as shown in FIG. 3 through FIG. 6.

As described above, in the second embodiment, a black-white image for showing a tumor portion without showing color blood fluid image is overlapped with a B mode cross sectional image so that a diseased area can be observed stereoscopically in a B mode cross-sectional image. Thus, diagnosis accuracy can be improved.

Although the invention has been explained in relation to its preferred embodiment, it is to be understood that many other possible modifications and variations can be made without departing from the spirit and scope of the invention.

For example, in the above embodiment, although a sector scanning method has been explained, a linear scanning method is applicable to the present invention. Although a point of sight in bird's-eye view has been located at a position of a probe of a B-mode cross sectional image, the point of sight can be located at any position. Although the MIP method has been explained as a method for forming a three dimensional image, other methods for displaying three dimensional image are applicable.

As described above, according to the present invention, one cross sectional surface is two dimensionally scanned under a scanning condition with a resolution level equal to or higher than that of a conventional two dimensional ultrasonic diagnosis device. An apparatus according to the present invention displays a cross sectional image with an echo brightness level equal to or greater than that of the picture image displayed by the conventional apparatus, obtains three dimensional information about a three dimensional region of which the scanned area is smaller than that of a conventional three dimensional ultrasonic diagnostic apparatus and a three dimensional image at least including the scanned region of the cross sectional image in order to overlap the three dimensional image on the cross sectional image. The three dimensional image may have a resolution/brightness less than that of the two-dimensional cross sectional image. In the case of mainly displaying the cross sectional view, there is provided a display method for standing the three dimensional image in bold relief on the cross sectional image so that it is possible to observe an image similar to an observation for diagnosing in a conventional two dimensional diagnostic apparatus and also information along a front-rear direction. Thus, an accurate diagnosis is judged easily. Further, in such a display, the cross sectional image is mainly indicated and the area three dimensionally scanned is very restricted compared to that of the conventional scanning so that it is possible to observe an image in real time.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ultrasonic diagnostic apparatus comprising:
    a probe having a two-dimensional array transducer scanning a three-dimensional regionin a body by transmitting an ultrasonic beam and receiving an ultrasonic echo signal;
    a transmitting/receiving circuit configured to drive the transducer to transmit an ultrasonic beam and to obtain two-dimensional cross sectional data corresponding to a two-dimensional cross sectional image and three-dimensional image information at a scan configuration in which the resolution of the two-dimensional image is higher than the resolution of the three-dimensional image information, the scan region for the three-dimensional image information is smaller than an area possible to scan by the apparatus, and the scan region for the three-dimensional cross sectional image is near the cross section from which the two-dimensional cross sectional image is obtained;
    a processor configured to produce a synthesized image from the two-dimensional cross sectional image data and the three-dimensional image information; and
    a display configured to display the three-dimensional image information overlapped on the two-dimensional cross sectional image in real time.

2. The apparatus of claim 1, wherein said three-dimensional image information obtained by said transmitting/receiving circuit is blood fluid information.

3. The apparatus of claim 1, wherein said three-dimensional image information obtained by said transmitting/receiving circuit is two-dimensional cross sectional information of a plurality of cross sectional surfaces.

4. The apparatus of claim 1, wherein said three-dimensional image information is obtained by said probe scanning a region of interest formed in said cross sectional image and extending along a direction perpendicular to said cross sectional image.

5. The apparatus of claim 4, wherein the region scanned by the probe in a direction perpendicular to said cross sectional image becomes smaller from a central position to a peripheral position in said region of interest.

6. The apparatus of claim 1, wherein said three-dimensional image information obtained by said transmitting/receiving circuit is information about a plurality of cross sectional surfaces located at a front side of said cross sectional image and a plurality of cross sectional surfaces located at a rear side of said cross sectional image.

7. The apparatus of claim 1, wherein said three-dimensional image information obtained by said transmitting/receiving circuit is information about a plurality of cross sectional surfaces located at a front side of said cross sectional image.

8. The apparatus of claim 1, wherein said display displays a mapping image of said three-dimensional image information overlapped with said cross sectional image.

9. The apparatus of claim 1, wherein said display displays a supplemental frame for showing said mapping image.

10. The apparatus of claim 1, wherein said display comprises a mode selection device for selecting a first mode for displaying only said cross sectional image, a second mode for displaying only said three-dimensional image information, and a third mode for displaying said three-dimensional image information overlapped with said cross sectional image.

11. The apparatus of claim 1, wherein said mode selection device comprises a switch configured to select one of the first mode through third modes.

12. The apparatus of claim 1, wherein said probe comprises a two-dimensional array of piezoelectric transducers.

13. The apparatus of claim 1, wherein the transmitting/receiving circuit obtains said three-dimensional image information in a first 3D scanning region defined by a plurality of cross sectional surfaces in front of and in a direction perpendicular to said two-dimensional cross sectional image and each of said cross sectional surfaces has an area smaller than that of said two-dimensional cross sectional image.

14. The apparatus of claim 13, wherein the transmitting/receiving circuit further obtains said three-dimensional image information in a second 3D scanning region defined by a plurality of cross sectional surfaces in back of and in a direction perpendicular to said two-dimensional cross sectional image and each of said cross sectional surfaces of said second scanned 3D region has an area smaller than that of said two-dimensional cross sectional image.

15. The apparatus of claim 14, wherein the cross sectional surfaces of said first and second 3D scanning regions have cross sectional areas which remain the same or decrease in size as the distance from the gray scale two dimensional cross sectional image increases.

16. The apparatus of claim 1, wherein said transmitting/receiving circuit comprises a first mechanism configured to obtain color doppler three-dimensional image information and a second mechanism configured to obtain a gray scale two-dimensional cross sectional image, and said display displays said color doppler three-dimensional image information embossed on said gray scale two-dimensional cross sectional image.

17. The apparatus of claim 16, wherein the transmitting/receiving circuit obtains said color doppler information in a first 3D scanning region defined by a plurality of cross sectional surfaces in front of and in a direction perpendicular to said gray scale cross sectional image and each of said cross sectional surfaces has an area smaller than that of said gray scale two-dimensional cross sectional image.

18. The apparatus of claim 17, wherein the transmitting/receiving circuit further obtains said color doppler information in a second 3D scanning region defined by a plurality of cross sectional surfaces in back of and in a direction perpendicular to said gray scale two-dimensional cross sectional image and each of said cross sectional surfaces of said second scanned 3D region is smaller than that of said gray scale two-dimensional cross sectional image.

19. The apparatus of claim 18, wherein the cross sectional surfaces of said first and second 3D scanning regions have cross sectional areas which remain the same or decrease in size as the distance from the gray scale two dimensional cross sectional image increases.

20. The apparatus of claim 1, wherein said transmitting/receiving circuit obtains said three-dimensional image information at a time different than when said two-dimensional cross sectional image is obtained.

21. The apparatus of claim 1, wherein said display comprises a mode selecting device for selecting between a first display mode in which the cross sectional image is displayed without the three-dimensional image information and a second display mode in which the three-dimensional image information is displayed overlapped with the cross sectional image.

22. The apparatus of claim 1, wherein the three-dimensional image information is obtained by scanning a three-dimensional region having a thickness of approximately 4 cm.

* * * * *